United States Patent
Kim

(10) Patent No.: US 10,624,593 B2
(45) Date of Patent: Apr. 21, 2020

(54) SYSTEMS FOR A PHOTOMULTIPLIER

(71) Applicant: General Electric Company, Schenectady, NY (US)

(72) Inventor: Chang Lyong Kim, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 10 days.

(21) Appl. No.: 15/725,033

(22) Filed: Oct. 4, 2017

(65) Prior Publication Data

US 2019/0099138 A1 Apr. 4, 2019

(51) Int. Cl.
| | | |
|---|---|---|
| H01L 21/02 | (2006.01) | |
| A61B 6/00 | (2006.01) | |
| G01T 1/208 | (2006.01) | |
| G01T 1/20 | (2006.01) | |
| A61B 6/03 | (2006.01) | |
| G01T 1/29 | (2006.01) | |
| H01L 27/146 | (2006.01) | |

(52) U.S. Cl.
CPC ............ *A61B 6/4241* (2013.01); *A61B 6/037* (2013.01); *A61B 6/4233* (2013.01); *G01T 1/208* (2013.01); *G01T 1/2018* (2013.01); *G01T 1/2985* (2013.01); *H01L 27/14663* (2013.01)

(58) Field of Classification Search
CPC .......................................... H01L 2224/48091
See application file for complete search history.

(56) References Cited

U.S. PATENT DOCUMENTS

| | | | |
|---|---|---|---|
| 7,652,257 B2 | 1/2010 | Li et al. | |
| 8,467,644 B1* | 6/2013 | Kim | G01T 1/2018 |
| | | | 362/610 |
| 2006/0163485 A1 | 7/2006 | Stearns et al. | |
| 2012/0153420 A1* | 6/2012 | Lee | G01T 1/2002 |
| | | | 257/432 |
| 2013/0249035 A1* | 9/2013 | Hedler | G01T 1/2018 |
| | | | 257/432 |
| 2013/0327932 A1 | 12/2013 | Kim et al. | |
| 2014/0110810 A1* | 4/2014 | Yamamoto | H01L 27/1443 |
| | | | 257/443 |

OTHER PUBLICATIONS

"Thermal effects of substrate materials used in the laser curing of particulate silver inks", Laser Assisted Net Shape Engineering 5, to Fearon et al., published Jan. 2007 (Year: 2007).*

Donati, S. et al., "Microconcentrators to recover fill-factor in image photodetectors with pixel on-board processing circuits," Optics Express, vol. 15, No. 26, Dec. 24, 2007, 10 pages.

(Continued)

*Primary Examiner* — Kenneth J Malkowski
(74) *Attorney, Agent, or Firm* — McCoy Russell LLP

(57) ABSTRACT

Systems are provided for a photomultiplier device. In one embodiment, a photomultiplier device includes a microcell including an active area coupled to a quenching resistor and a signal line coupled to the quenching resistor, the signal line including a first side surface, a second side surface, and a base, the first side surface and second side surface angled inward toward each other.

13 Claims, 6 Drawing Sheets

(56) References Cited

OTHER PUBLICATIONS

Lee, C. "Design and Fabrication of PDE enhanced SiPM with Mircro-lens," Proceedings of the 8th International Conference on Position Sensitive Detectors, Sep. 4, 2008, University of Glasgow, Glasgow, Scotland, 1 page.
Barton, P. et al., "Effect of SSPM Surface Coating on Light Collection Efficiency and Optical Crosstalk for Scintillation Detection," Nuclear Instruments and Methods in Physics Research Section A: Accelerators, Spectrometers, Detectors and Associated Equipment, vol. 610, No. 1, Oct. 2009, 6 pages.
Intermite, G. et al., "Fill-factor improvement of Si CMOS single-photon avalanche diode detector arrays by integration of diffractive microlens arrays," Optics Express, vol. 23, No. 26, Dec. 22, 2015, 15 pages.
"Microcell Construction," KETEK Website, Available Online at https://www.ketek.net/sipm/technology/microcell-construction/, Available as Early as May 8, 2017, 3 pages.

\* cited by examiner

SYSTEMS FOR A PHOTOMULTIPLIER

FIELD

Embodiments of the subject matter disclosed herein relate to medical imaging, and more particularly, to photomultipliers for medical imaging detectors.

BACKGROUND

PET detectors may have a scintillator component and a photodiode component, where the scintillator component illuminates upon reception of radiation energy and the photodiode detects illumination of the scintillator component and provides an electrical signal as a function of the intensity of illumination. In such a configuration, the scintillators may be coupled to a solid-state photomultiplier (SSPM). The SSPM is comprised of a plurality of Geiger-mode avalanche photodiodes (APDs) or "microcells" that amplify each single optical photon from the scintillator into a large and fast signal current pulse.

In some examples, the microcells may be arranged into an array. Each microcell output may be connected to a signal line through a respective quenching resistor. These plurality of signal lines and resistors traversing the array represent non-active (e.g., non-photosensitive) areas of the photomultiplier that reduce the photon detection efficiency of the detectors.

BRIEF DESCRIPTION

In one embodiment, a photomultiplier device includes a microcell including an active area coupled to a quenching resistor and a signal line coupled to the quenching resistor. The signal line includes a first side surface, a second side surface, and a base. The first side surface and second side surface are angled inward toward each other. In this way, the side surfaces of the signal line may act to reflect incident photons back to the active area.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
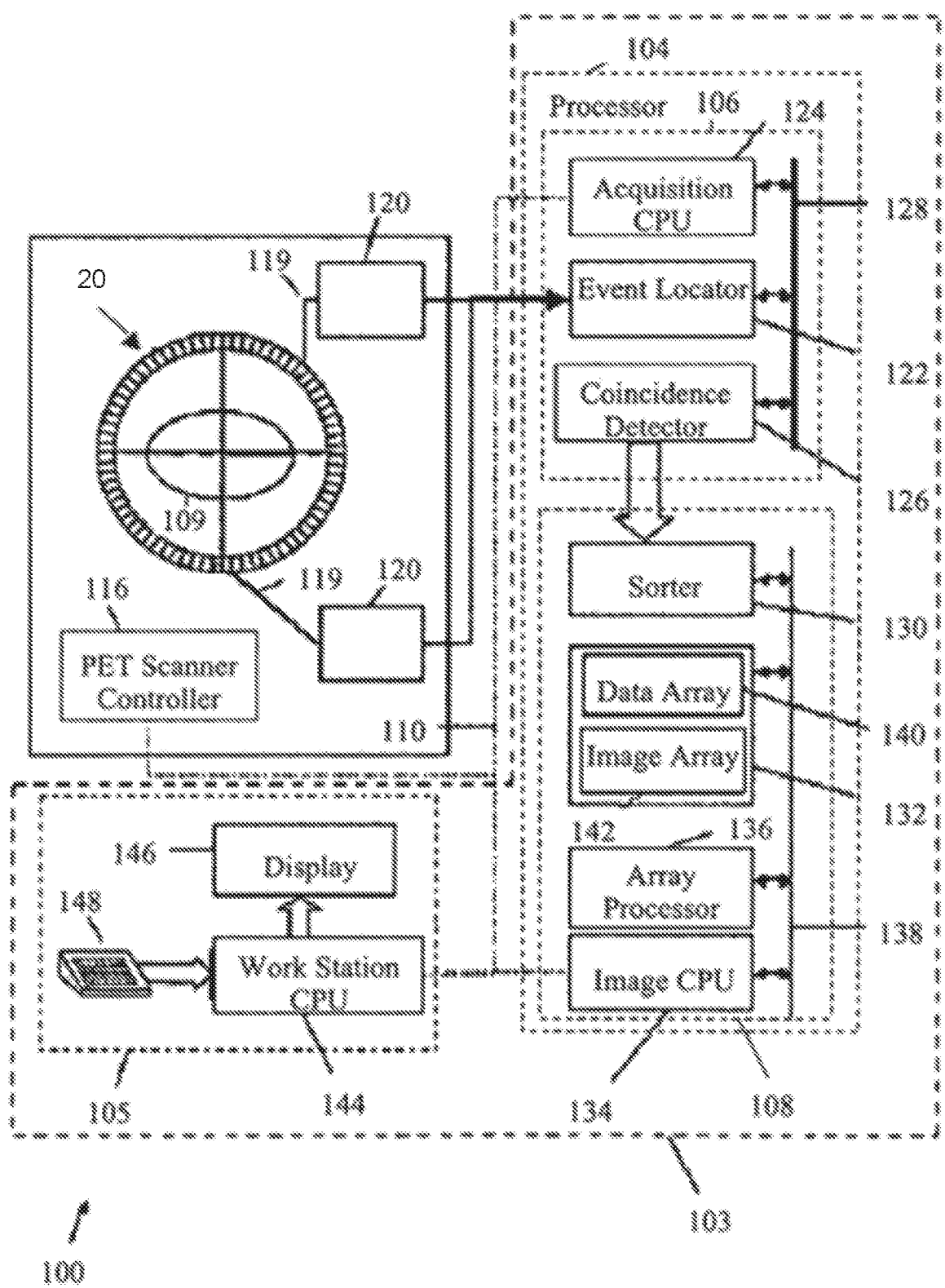
FIG. 1 is a block diagram of a PET imaging system.

The following description relates to various embodiments of a photomultiplier device (such as a solid state photomultiplier, referred to as an SSPM) of a radiation detector. In particular, systems and methods are provided for increasing the photon detection efficiency of the detector by redirecting photons that impinge on the inactive areas of the photomultiplier device to active areas, without increasing the cost or manufacturing complexity of the photomultiplier device.

A silicon photomultiplier (SiPM) device may include 100-10000 microcells of the size of 25 um×25 um to 100 um×100 um. Each microcell output is connected to a signal collection line through a quenching resistor. The quenching resistor and signal/bias lines are not active (photosensitive) areas. Thus, even as efforts to increase the quantum efficiency of the microcell active areas have been successful, the photon detection efficiency (PDE) of the microcells is still limited by the relatively high area taken up by the inactive areas.

Other attempts to increase the PDE by reducing the effect of the non-active areas have included the addition of microlenses, flat reflective coatings on the non-active areas, and shaped reflective areas built on top of the inactive areas to redirect the light/photons in an inactive area toward an active area. However, each of these configurations has drawbacks that make implementation difficult. For example, building a separate structure on top of the inactive areas is a complex process that adds significant cost. Simply adding a reflective coating on the (otherwise flat) inactive areas is also problematic, as the light reflects from the coating back to the scintillation crystals first before travelling toward an active area. These photons travel longer distance with some absorption probability. Since these photons come later than the initial fast photons, such a configuration does not to improve timing resolution. Finally, adding micro-lenses increases manufacture cost and complexity and the optical glue used to attach the micro-lens to the SiPM and scintillation crystals has a similar refractive index of a micro-lens made of glass, thus greatly diminishing the focusing function.

Thus, as described in more detail herein, the 3D shape of conductive signal lines and quenching resistors themselves may be used to redirect injected photons toward the active areas, by using photolithography technology that is capable of 3D patterning. Rather than building a separate structure as discussed above, a reflective surface structure of the SiPM components are formed directly, by utilizing the photolithography technology that can make a shaped structure. In doing so, manufactured costs may be lowered relative to building a separate structure and focusing or other light effects that may be introduced by coupling separate structures to the SiPM may be avoided.

The SiPM disclosed herein may be integrated into any number of radiation detection devices, including gamma spectrometers/isotope identifiers, neutron detectors, computed tomography systems, and positron emission tomography (PET) systems.

FIG. 1 is a block diagram of an exemplary embodiment of a PET system 100 in which various embodiments of the disclosure may be implemented. PET system 100 includes a detector ring assembly 20. PET system 100 further includes a controller 103 to control data acquisition and image reconstruction processes. Controller 103 includes a processor 104 and an operator workstation 105. Processor 104 includes a data acquisition processor 106 and an image reconstruction processor 108, which are interconnected via a communication link 110. PET system 100 acquires scan data and transmits the data to data acquisition processor 106. The scanning operation is controlled from operator workstation 105. The data acquired by data acquisition processor 106 is reconstructed using image reconstruction processor 108.

Detector ring assembly 20 includes a central opening, in which an object 109 may be positioned, using, for example, a motorized table, that is aligned with the central axis of detector assembly 20. This motorized table moves object 109 into the central opening of detector ring assembly 20 in response to one or more commands received from operator workstation 105. A PET scanner controller 116, also referred to as the gantry controller, is provided (e.g., mounted) within PET system 100. PET scanner controller 116 responds to the commands received from operator workstation 105 through communication link 110. Therefore, the scanning operation is controlled from operator workstation 105 through PET scanner controller 116.

Detector ring assembly 20 includes a plurality of detector units arranged in one or more detector rings. Each detector unit includes a set of scintillator crystals arranged in a matrix that is disposed in front of a silicon photomultiplier cell array (described in more detail below). When a photon collides with a crystal on a detector, it produces a scintilla on the crystal. A cell of the silicon photomultiplier array produces an analog signal on communication line 119 when a scintillation event occurs. A set of acquisition circuits 120 is provided to receive these analog signals. Acquisition circuits 120 produce digital signals indicating the gamma ray interaction location and total energy of the event. Acquisition circuits 120 also produce an event detection pulse, which indicates the time or moment the scintillation event occurred. These digital signals are transmitted through a communication link, for example, a cable, to an event locator circuit 122 in data acquisition processor 106.

Data acquisition processor 106 includes event locator circuit 122, an acquisition CPU 124, and a coincidence detector 126. Data acquisition processor 106 periodically samples the signals produced by acquisition circuits 120. Acquisition CPU 124 controls communications on a back-plane bus 128 and on communication link 110. Event locator circuit 122 processes the information regarding each valid event and provides a set of digital numbers or values indicative of the detected event. For example, this information indicates when the event took place and the position of the scintillation crystal that detected the event. An event data packet is communicated to coincidence detector 126 through back-plane bus 128. Coincidence detector 126 receives the event data packets from event locator circuit 122 and determines if any two of the detected events are in coincidence. Coincidence is determined by a number of factors. First, the time markers in each event data packet must be within a predetermined time period, for example, 4.5 nanoseconds, of each other. Second, the line of response (LOR) formed by a straight line joining the two detectors that detect the coincidence event should pass through the field of view in PET system 100. Events that cannot be paired are discarded. Coincident event pairs are located and recorded as a coincidence data packet that is communicated through a communication link to a sorter 130 in image reconstruction processor 108.

Image reconstruction processor 108 includes sorter 130, a memory module 132, an image CPU 134, an array processor 136, and a back-plane bus 138. Sorter 130 counts all events occurring along each projection ray and organizes them into 4D data. This 4l) data (or sinograms) is organized in one exemplary embodiment as a data array 140. Data array 140 is stored in memory module 132. Back-plane bus 138 is linked to communication lurk 110 through Image CPU 134. Image CPU 134 controls communication through backplane bus 138. Array processor 136 is also connected to back-plane bus 138. Array processor 136 receives data array 140 as an input and reconstructs images in the form of image arrays 142. Resulting image arrays 142 are stored in memory module 132.

The images stored in image array 142 are communicated by image CPU 134 to operator workstation 105. Operator workstation 105 includes a CPU 144, a display device 146 and an input device 148. CPU 144 connects to communication link 110 and receives inputs (e.g., user commands) from input device 148. Input device 148 may be, for example, a keyboard, mouse, or a touch-screen panel. Through input device 148 and associated control panel switches, the operator can control the calibration of PET system 100 and the positioning of object 109 for a scan. Similarly, the operator can control the display of the resulting image on display device 146 and perform image-enhancement functions using programs executed by workstation CPU 144.

In general, the data array received by array processor 136 has to be corrected before being reconstructed. This level of correction includes normalization, scatter correction, and geometrical calibration.

Figure 2:
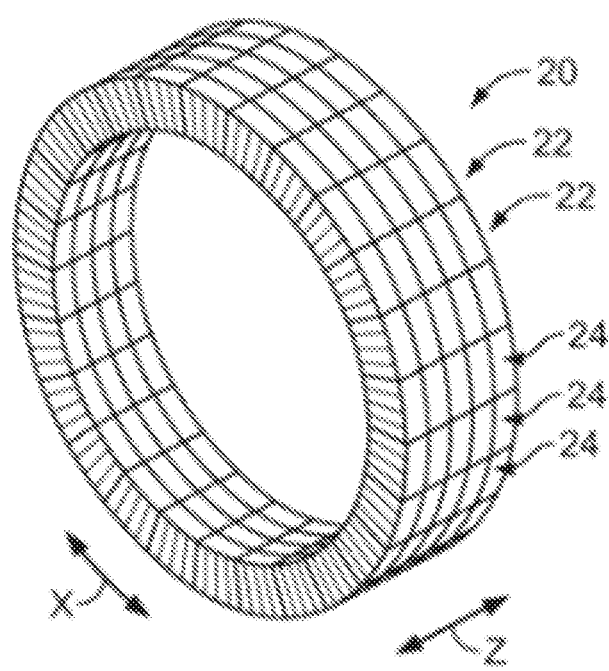
FIG. 2 schematically shows an example detector ring assembly.

FIG. 2 shows the PET detector ring assembly 20, which includes a plurality of detector modules 22 that are arranged in a ring to form the PET detector ring assembly 20. Each detector module 22 is assembled from a plurality of detector units 24. Thus, a plurality of detector units 24 is assembled to form a single detector module 22, and a plurality of detector modules 22 is assembled to form the detector ring assembly 20. In one embodiment, the detector ring assembly 20 includes twenty-eight detector modules 22 that are coupled together such that the detector ring assembly 20 has a brig shape. In some embodiments, each detector module 22 includes twenty detector units 24 that are arranged in a 4×5 matrix. It should be realized that the quantity of detector modules 22 utilized to form the detector ring assembly 20 is exemplary, and that the detector ring assembly 20 may have more than or fewer than twenty-eight detector modules 22. Moreover, it should be realized that quantity of detector units 24 utilized to form each detector module 22 is exemplary, and that the detector module 22 may have more than or fewer than twenty detector units 24.

Figure 3:
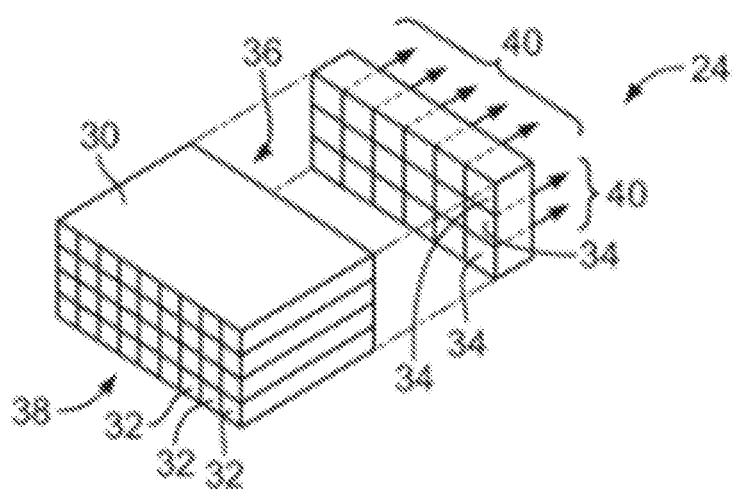
FIG. 3 schematically shows an example detector unit.

FIG. 3 is a perspective view of an exemplary detector unit 24 that may form a portion of the detector ring module 22 shown in FIG. 2. In various embodiments, the detector unit 24 includes a scintillator block 30 having one or more scintillator crystals 32 that are arranged along an x-axis and a z-axis. In one embodiment, the scintillator block 30 has thirty-six crystals 32 that are arranged in a 4×9 matrix. However, it should be realized that the scintillator block 30 may have fewer than or more than thirty-six crystals 32, and that the crystals 32 may be arranged in a matrix of any suitable size. It also should be noted that the scintillator crystals 32 may be formed from any suitable material such as bismuth germinate (BGO), Cerium-doped Lutetium Yttrium Orthosilicate (LYSO) or Gadolinium Oxyorthosilicate (GSO), among others.

The detector unit 24 also includes a plurality of light sensors 34, illustrated as a plurality of photosensors, which may be any suitable photo-detectors that sense or detect light or other electromagnetic energy. In the illustrated embodiment, the light sensors 34 are silicon photomultipliers (SIPMs). The plurality of light sensors 34 are coupled at an end of the scintillator block 30 opposite a detector face 38. The surfaces of the crystal block 30 not coupled to the light sensors 34 are covered with a reflective layer such as polytetrafluoroethylene, TiO2 load epoxy, or a spectral reflector. It should be noted that in some embodiments, a reflector or reflective material may be placed between some crystals in the crystal block 30.

In various embodiments, the detector unit 24 has eighteen light sensors 34 on each end of the scintillator block 30 that are arranged in a 3×6 matrix. However, it should be realized that the detector unit 24 may have fewer than or more than eighteen light sensors 34 and that the light sensors 34 may be arranged in a matrix of any suitable size. For example, some embodiments include 36, 54 or 100 crystals 32 having corresponding light sensors 34 that are arranged in a 6×6 matrix, 9×6 matrix or 10×10 matrix, respectively. It should be noted that in various embodiments, a one-to-one coupling between the light sensor 34 (e.g., a photosensor) and the crystal 32 is not provided, such that there is a one-to-multiple coupling between the light sensor 34 and the crystal 32. However, in other embodiments, a one-to-one coupling between the light sensor 34 (e.g., a photosensor) and the crystal 32 may be provided. Also, the light sensors 34 may have a different size or shape. In some embodiments, the light sensors 34 are larger than 3×3 mm$^2$. However, in other embodiments, larger or smaller light sensors 34 may be used such as 4×6 mm$^2$ light sensors 34.

In one embodiment, the light sensors 34 are avalanche photodiodes that are connected in parallel and operated above a breakdown voltage in a Geiger mode. For example, the light sensors 34 may be SIPMs ire various embodiments that are configured as single photon sensitive devices formed from an avalanche photodiode array on a silicon substrate.

In operation, the scintillator crystals 32 convert the energy, deposited by a gamma ray impinging on the scintillator crystal 32, into visible (or near-UV) light photons. The photons are then converted to electrical analog signals by the light sensors 34. More specifically, when a gamma ray impinges on any one of the scintillator crystals 32 in a detector unit 24, the scintillator detecting the gamma ray converts the energy of the gamma ray into visible light that is detected by the light sensors 34 in the detector unit 24. Thus, in the exemplary embodiment, each detector unit 24 is configured to output "n" analog signals 40.

Figure 4:
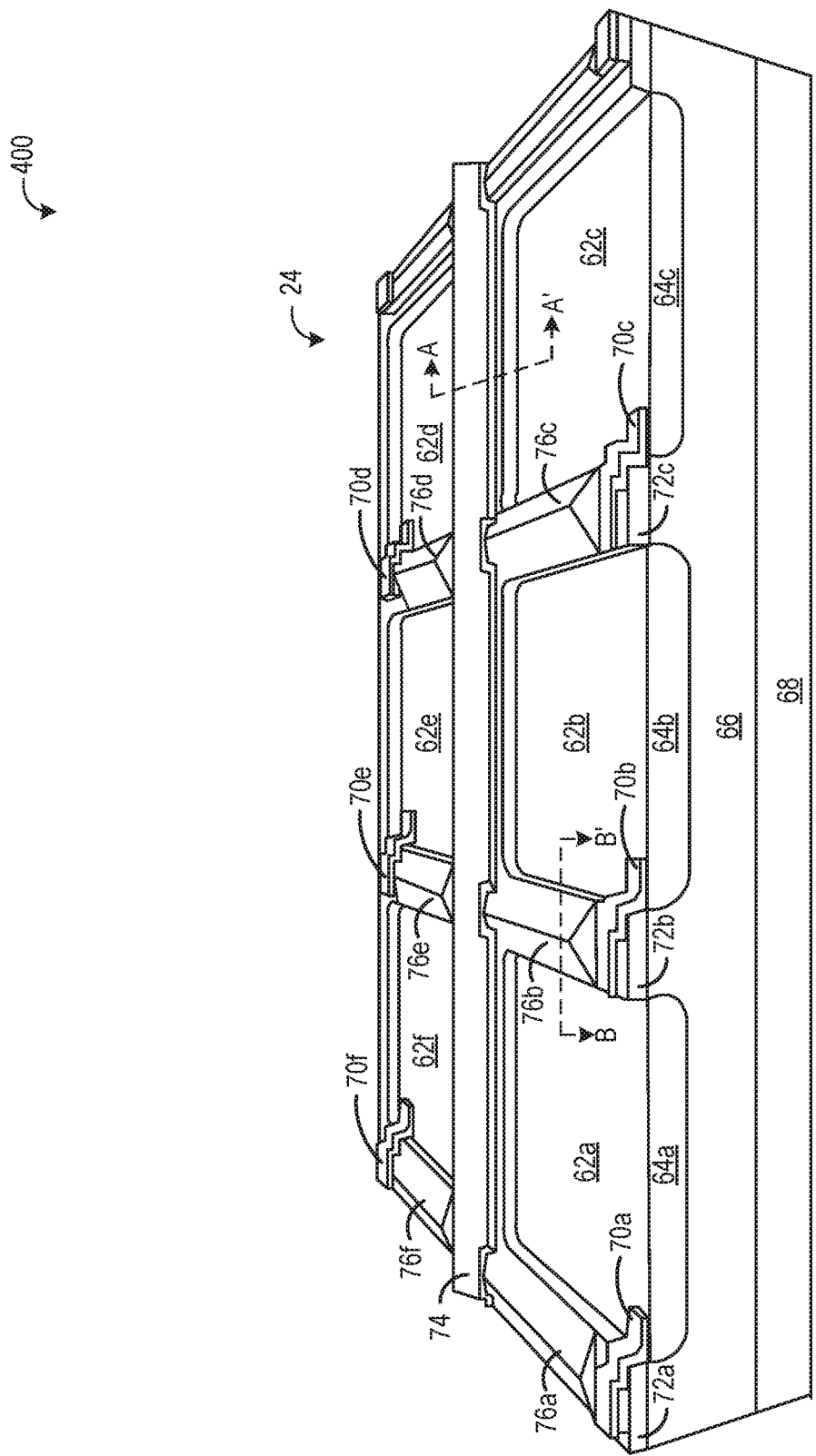
FIG. 4 is a cross-sectional view of an embodiment of microcell array.

A portion of a detector unit 24 is shown in FIG. 4 as being comprised of a plurality of avalanche photodiodes (APDs) or "microcells" that amplify single optical photon arrivals from the scintillator into a large signal. FIG. 4 illustrates six microcells 62a-62f. Typically, each detector unit will include between 100 to 2500 APDs per mm$^2$, with each of the microcells having a length of 20-100 microns. Each of the microcells operates as an individual Geiger-mode APD a few volts above a breakdown voltage, with each microcell being virtually identical to all the other microcells. In this mode of operation, an electron generated by the absorption of an optical photon initiates an avalanche breakdown that is confined to an individual microcell when the one or more photons is absorbed by that microcell. A single discrete unit of electrical charge is emitted from the microcell independent of the number of photons absorbed therein. That is, for each Geiger breakdown, the output signal of the microcell will have the same shape and charge, except for small variations due to differences from cell to cell in PN junction structure introduced in the production process.

Each microcell of the pixel is positioned on a common N-doped silicon substrate 68, although P-doped substrates are also possible. Each microcell includes an entrance window (also referred to as an active area) comprised of P-doped. This forms a p-n junction (e.g., of a p-on-n configuration). During use, a depletion region 66 is created. The depletion region is an insulating region where the mobile charge carriers have been diffused away, or have been forced away by an electric field. This may occur when the p-type dopant with acceptor impurities (excess holes), comes into contact with the n-type silicon, doped with donor impurities (excess electrons) and the holes and the electrons flow across the junction into lower potential areas on the opposite side of the junction.

Thus, microcell 62a includes entrance window 64a, microcell 62b includes entrance window 64b, microcell 62c includes entrance window 64c, microcell 62d includes entrance window 64d, microcell 62e includes entrance window 64e, and microcell 62f includes entrance window 64f. Each entrance window may include an anti-reflective layer, comprised of silicon nitride, for example.

Figure 5:
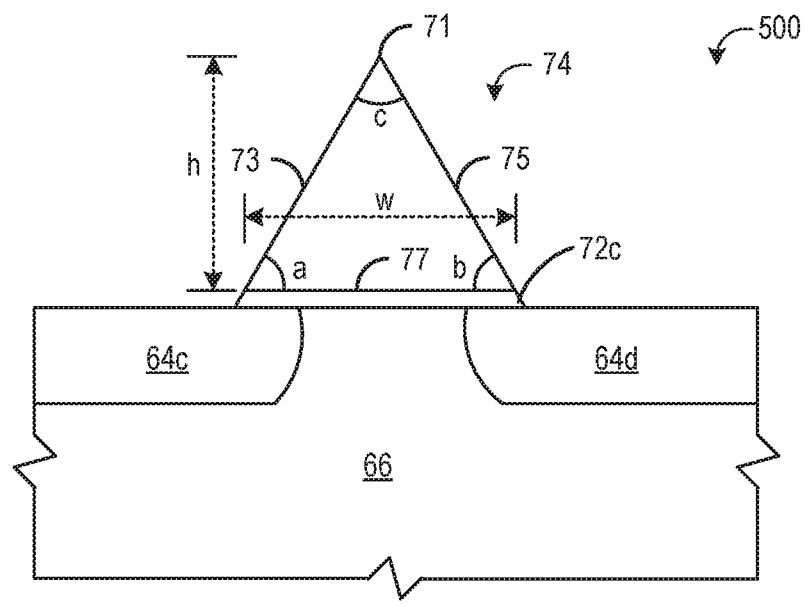
FIG. 5 is a first cross-sectional view of the microcell array of FIG. 4.

The active areas of the microcell a are each surrounded by photon-insensitive inactive areas, which electrically isolate the microcells from each other and may also accommodate contact lines for bias and/or signal contacts and in some cases other features such as poly-silicon or metal quench resistors, transistors, optical isolation trenches, or guard structures. As shown, each microcell is surrounded by a respective silicon dioxide insulator. Microcell 62a is surrounded by insulator 72a, microcell 62b is surrounded by insulator 72h, and microcell 62c is surrounded by insulator 72c. It is to be appreciated that the remaining microcells illustrated in FIG. 5 are likewise surrounded by insulators that are not visible in FIG. 5. Further, the insulators are given separate reference numbers for clarity, but it is to be understood that the insulators may comprise integrated/continuous components and may not be discrete insulators, and that differently numbered insulators may share overlapping components.

Each microcell is connected to a signal line, such as signal line 74, on the front side of the detector unit. In one embodiment, the signal line 74 is comprised of aluminum, although other similar materials are also envisioned that are conductive and also non-magnetic, at least in some examples. Connection between the active area of each microcell and a corresponding signal line is formed by way of a quenching resistor, comprised of polysilicon in one embodiment and metal resistor in another embodiment. The resistor is connected to the active area of the microcell by way of a contact and serves to quench the avalanche in the microcell once the cell capacitance discharges. Thus, microcell 62a is coupled to signal line 74 via contact 70a and resistor 76a, microcell 62b is coupled to signal line 74 via contact 70b and resistor 761, microcell 62c is coupled to signal line 74 via contact 70c and resistor 76c, microcell 62d is coupled to signal line 74 via contact 70d and resistor 76d, microcell 62e is coupled to signal line 74 via contact 70e and resistor 76e, and microcell 62f is coupled to signal line 74 via contact 70f and resistor 76f.

While only six microcells and one signal line are illustrated in FIG. 4, it is to be understood that the detector unit may include a plurality of additional microcells (such as 3600 microcells for an array comprised of 50×50 micron microcells). A plurality of additional signal lines may be present, such as one signal line for every row of microcells or one signal line for every two rows of microcells.

By way of resistors and signal lines, the independently operating APD cells are electrically connected, and the individual outputs of all the microcells are summed to form a common readout signal. The common readout signal that is output from the detector unit, shown in FIG. 4, is thus the superposition of the standardized signals of all tired microcells. That is, the output of each detector unit is determined by the sum of the discrete electrical charge units from the microcells that fire. As such, the output of the detector unit of FIG. 4 is dependent on the number of microcells that absorb a photon rather than the number of photons absorbed by each microcell. Under operation conditions in which the number of absorbed photons is below the number of microcells, the resulting output from each detector unit is in the form of an analog pulse with a charge that is proportional to the number of absorbed photons.

Thus, a silicon photomultiplier (SiPM) device such as the device illustrated in FIG. 4 may include of 100-10,000 microcells of the size of 25 um×25 um to 100 um×100 um. Each microcell output is connected to a signal collection line through a quenching resistor in case of passive quenching. For active quenching, a digital circuit senses an avalanche and generates a corresponding digital (e.g., CMOS, transistor-transistor logic) output that is fed to a signal collection line. The quenching resistor, digital circuits, and signal/bias lines are not active (photosensitive) areas. The active area decreases as a microcell size decreases, since the gap or width of the inactive area between two microcells is independent of microcell size. So the relative size of the inactive area around a microcell increases when a microcell gets smaller. As a result, while the quantum efficiency of the active area may reach 81% and above, the small fill factor of 61.5% reduces photon detection efficiency (PDE) to 81%×61.5%=50% in 50 um×50 um microcell SiPM. The 25 um×25 um microcells with 30% of fill factor would have a PDE of 81%×30%=24.3%.

SiPM operates above PN junction breakdown voltage. When a charge avalanche occurs with an injection of a single photon, the current starts flowing through the quenching resistor and induces voltage drop across the resistor, in a passive quenching SiPM. The voltage drop brings down the microcell voltage below its breakdown voltage, which stops/quenches the current flow. Then, microcell recharge starts and it takes $C_{microcell}*R_{quench}$ recover time, which could take 20 nanoseconds to 1 microsecond depending on the size of $C_{microcell}$ and $R_{quench}$. To reduce the long recovery time after avalanche, an active quenching circuit may be used, which may include a current flow sensing circuit, microcell voltage control circuit (e.g., quenching circuit), and a recharge circuit. The whole circuit can be made of two to six transistors. In the case of an active quenching circuit, at least one additional power line may be present for the electronics, and these additional power lines may be shaped in the manner described herein (e.g., triangular) in order to redirect light/photons to an active area.

In order to increase PDE, which is valuable for timing resolution, the light/photons in an inactive area may be redirected toward an active area. According to embodiments disclosed herein, the 3D shape of the conductive signal lines and quenching resistors may be used to redirect injected photons toward the active area. Using photolithography technology that is capable of 3D patterning, the signal lines and quenching resistors may be of triangular, trapezoidal, or other shape. In doing so, the additional reflective surface area provided by the signal lines and resistors may redirect photons that are initially directed to the signal lines and resistors to a nearby active region. By utilizing the structure of the photomultiplier itself, rather than adding additional separate structure on top of the photomultiplier, the manufacturing process costs and complexity may be reduced.

The signal lines and resistors may have a suitable 3D shape that is adapted to redirect incident photons to a nearby/underlying active area. As such, the signal lines and resistors may have side surfaces that are sloped/angled inward. For example, a signal line may include a base that is in face-sharing contact with an insulator, where the insulator is positioned on a microcell array over an inactive area (e.g., the area between two adjacent active areas). The signal line may include a first side surface that extends vertically and intersects the base and a second side surface that extends vertically, intersects the base, and is opposite the first side surface. The first side surface and second side surface may angle inward, e.g., toward each other. As such, the signal line may include a first internal angle between the first side surface and the base that is less than 90° and a second internal angle between the second side surface and base that is less than 90°. In some examples, the signal line may include a top surface, resulting in the signal line having a cross-sectional shape of a parallelogram. In other examples, the signal line may not include a flat top surface, resulting in the signal line having a triangular or rounded triangular cross-sectional shape. Similar parameters apply to the resistors, as described in more detail below.

Figure 6:
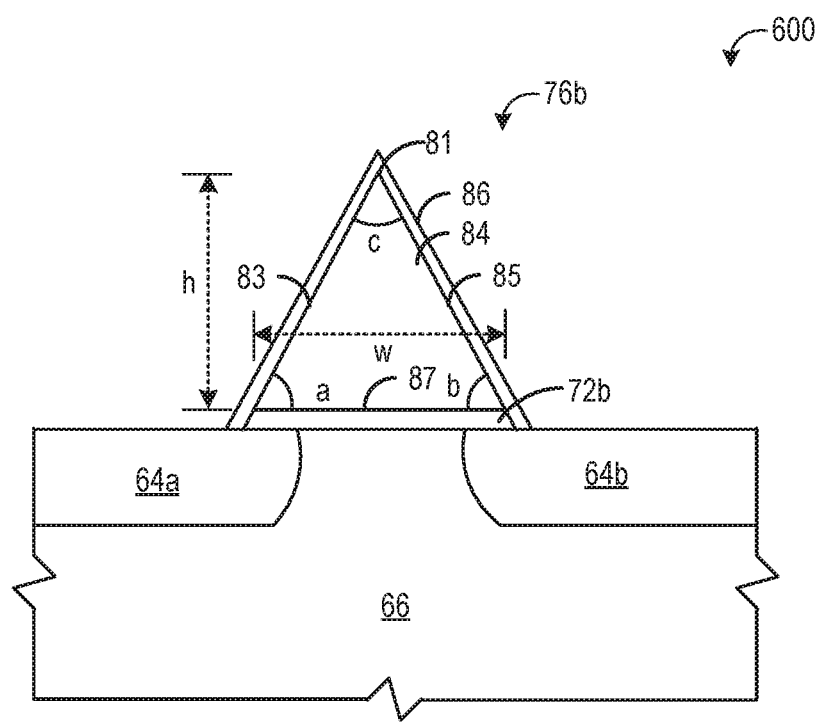
FIG. 6 is a second cross-section view of the microcell array of FIG. 4.

The cross-section shape of the signal line 74 and a representative resistor 76*b* are shown in FIGS. 5 and 6, respectively. FIG. 5 is a cross-sectional view 500 of a portion of detector unit 24 taken across lines A-A' of FIG. 4. Signal line 74 is positioned on insulator 72*c* and entrance windows 64*c* and 64*d*. The signal line 74 includes a base 77, first side surface 73, and second side surface 75. Signal line 74 has a triangular cross-sectional shape. The triangular cross-sectional shape of signal line 74 includes a peak 71 that is vertically above the array of microcells, where the peak is positioned above the underlying insulator 72*c* by a height h. The signal line 74 has width w at its base (e.g., where the signal line couples to the insulator). The first side surface and second side surface are angled inward, such that internal angle a and internal angle b are each less than 90°.

In the example shown, the triangle is an equilateral triangle with three 60° angles (e.g., angles a, b, and c are the same), although other angles are possible. In some examples, each angle of the triangle may be selected to provide desired reflectance. In one example, the angles of the triangle may be selected based on a size of the microcell. For example, larger/steeper angles may be selected for a smaller microcell (e.g., wherein an area of the entrance window is smaller) relative to a larger microcell, in order to direct as many incident photons from the inactive area to the active area. As such, in the example presented in FIG. 5, the angles of the signal line 74 where the signal line couples to the microcells (e.g., angles a and b) may be increased relative to 60° if the microcells are larger (such as to 75°) or decreased relative to 60° if the microcells are smaller (such as to 45°). The width of the base may be between 1 um and 6 um depending on the capability of photolithography. The height of the signal line structure may be equal to the width of the base or taller.

Signal line 74 may be comprised of aluminum, which has 90% reflectivity at 400 nm. Thus, the reflectivity of the aluminum may be utilized to redirect incident photons to the active area/entrance window by building the triangle shape of signal line as shown in FIG. 5. Due to the signal line being comprised of aluminum, no external reflective coating is used, lowering cost and complexity of the manufacturing process. However, other types of material may be used, such as copper containing materials. Further, the signal line may be of a shape other than triangular, as described in more detail below.

FIG. 5 shows the insulator 72c and signal line 74 extending over a portion of entrance window 64c and entrance window 64d. A lower PDE is expected at the edge of an active area than the center area, and thus the insulator and signal line can be extended over the edge of the entrance window to ensure the entirety of the inactive area is covered. As explained above, the insulator may be comprised of silicon dioxide, which is transparent as it is also used to make anti-reflective layers in the active area.

Additionally, by shaping the signal line into a triangular or other 3D shape, the signal line increases in thickness, which reduces the impendence (resistance and inductance) of the aluminum traces. By lowering the impedance, the transit time spread of signals among the microcells decreases, thus improving timing resolution for Time-of-Flight (TOF) PET.

FIG. 6 is a cross-sectional view 600 of a portion of detector unit 24 taken across lines B-B' of FIG. 4. Resistor 76b is positioned on insulator 72b and entrance windows 64a and 64b. Resistor 76b is comprised of a polysilicon core 84 and a reflective coating 86. The resistor 76b includes a base 87, first side surface 83, and second side surface 85. Resistor 76b has a triangular cross-sectional shape. The triangular cross-sectional shape of resistor 76b includes a peak 81 that is vertically above the array of microcells, where the peak is positioned above the underlying insulator 72b by a height h. The resistor 76b has width w at its base (e.g., where the resistor couples to the insulator). The first side surface and second side surface are angled inward, such that internal angle a and internal angle b are each less than 90°.

In the example shown, the triangle is an equilateral triangle with three 60° angles (e.g., angles a, b, and c are the same), although other angles are possible. In some examples, each angle of the triangle may be selected to provide desired reflectance. In one example, the angles of the triangle may be selected based on a size of the microcell. For example, larger/steeper angles may be selected for a smaller microcell (e.g., wherein an area of the entrance window is smaller) relative to a larger microcell, in order to direct as many incident photons from the inactive area to the active area. As such, in the example presented in FIG. 6, the angles of the resistor 76b where the resistor couples to the microcells (e.g., angles a and b) may be increased relative to 60° if the microcells are larger (such as to 75°) or decreased relative to 60° if the microcells are smaller (such as to 45°). The width of the base area may be between 1 um and 6 um depending on the capability of photolithography. The height of the resistor structure may be equal to the width of the base or taller.

Resistor 76b may be comprised of polysilicon, which has low reflectivity at 400 nm. Thus, the polysilicon core may be coated with a reflective coating to redirect incident photons to the active area/entrance window. The reflective coating may be comprised of silicon nitride. The thickness of the silicon nitride layers may be controlled to generate a reflective layer. In other examples, the reflective layer may be comprised of aluminum. In such an example, an insulating layer of silicon dioxide may be formed on the polysilicon core. Then, an aluminum layer may be deposited on top of silicon dioxide to make the surface of the resistor light reflective. In still further examples, the resistor may be comprised of metal (e.g., aluminum, tungsten) which has sufficient reflectivity to avoid the need for a reflective coating.

FIG. 6 shows the insulator 72b and resistor 76b extending over a portion of entrance window 64a and a portion of entrance window 64b. As explained above, the lower PDE is expected at the edge of an active area than the center area, and thus the insulator and resistor can be extended over the edge of the entrance window to ensure the entirety of the inactive area is covered.

Figure 7:
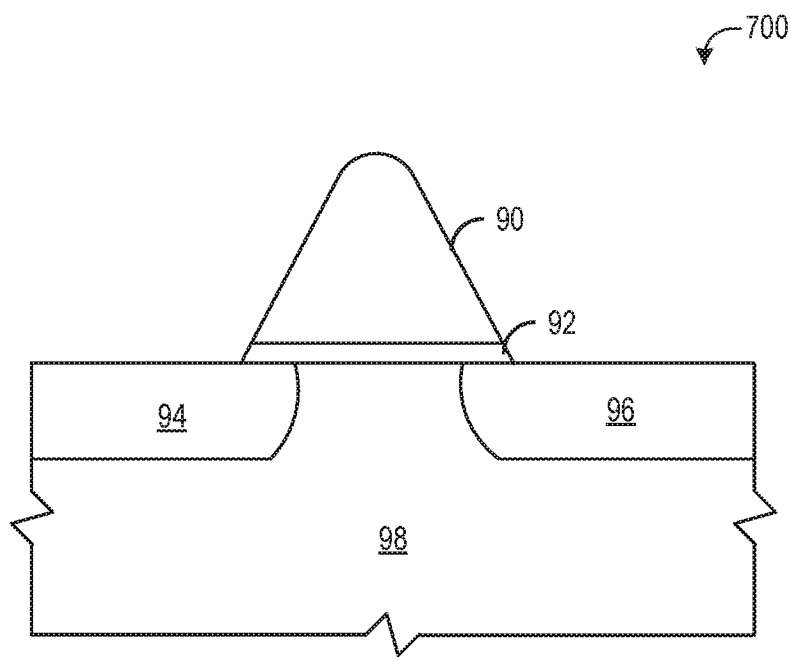
FIGS. 7 and 8 are cross-sectional views of additional embodiments of a microcell array.
Figure 8:
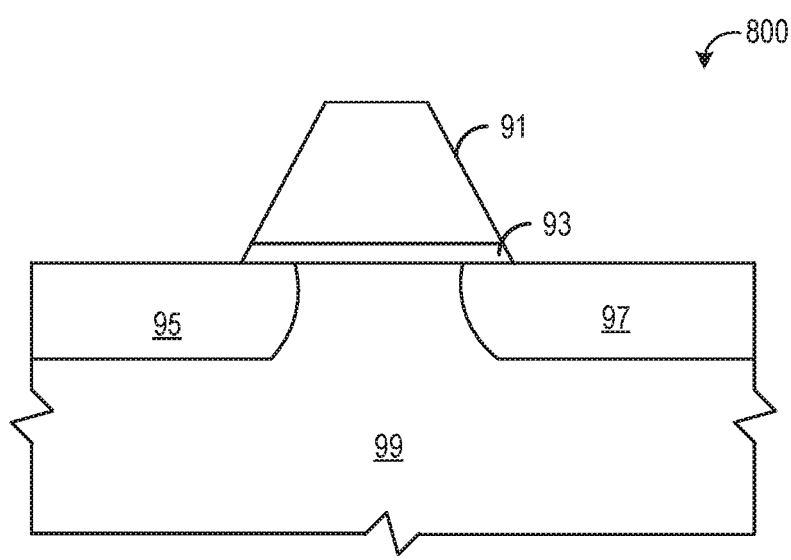

FIGS. 7 and 8 show additional example cross-sectional shapes that may be used rather than a triangular shape, for one or both of the signal line and resistor. FIG. 7 shows a cross-sectional view 700 of a first signal line 90 positioned on an insulator 92, which is positioned on a first entrance window 94, second entrance window 96, and a gap area in N doped base zone 98. FIG. 8 shows a cross-sectional view 800 of a second signal line 91 positioned on an insulator 93, which is positioned on a first entrance window 95, second entrance window 97, and a gap area in the base zone 99. Each of first signal line 90 and second signal line 91 are non-limiting examples of signal line 74. Further, the cross-sectional shapes shown in FIGS. 7 and 8 may apply to resistors in addition or alternative to signal lines.

As explained above, the signal lines (and resistors) may be manufactured using photolithography, which may make it challenging to produce the sharp corners of the triangular cross-sectional shapes shown in FIGS. 5 and 6. Thus, rather than use a strict triangular shape, the signal lines may have a parallelogram (as in the case of signal line 91) or a rounded triangle (as in the case of signal line 90) cross-sectional shape, which still allows a large fraction of the inactive area to redirect incident light to the active area. In the case of a parallelogram, the signal line includes a flat top surface. In the case of the rounded triangle, the signal line includes a curved top surface. The side surfaces may similar to the side surfaces described above with respect to FIG. 5, e.g., angled inward, to produce internal angles at the base of the signal line that are less than 90°.

Returning to FIG. 4, the signal line 74 may be a continuous line that runs without interruption from one side of the microcell array/pixel to the other side. The signal line 74 may be of triangular shape along the entirety of the signal line. Thus, the peak of the triangle may extend uninterrupted from one end of the microcell array to the other end. The signal line 74 intersects multiple resistors. As shown, signal line 74 intersects each of resistors 76a-76f. At each intersection, the signal line 74 is electrically coupled to a respective resistor.

Referring to resistor 76a as an example, resistor 76a is coupled to signal line 74. Likewise, resistors 76b-76f may each be coupled to signal line 74 (while not clearly visible in FIG. 4, it is to be understood that resistors 76a and 76f, for example, are not directly coupled to one another). At the intersection with signal line 74, rather than being triangular shaped, resistor 76a may be substantially flat. Signal line 74 may extend over the flat surface of resistor 76a. In this way, signal line 74 may be maintained triangular, even over the region where the signal line intersects a resistor. The resistor may be made flat in the region that intersects the signal line, but may be triangular in the remaining regions of the resistor. However, other configurations are possible, such as the resistors being triangular along their entirety and the signal line being made flat in the regions where the signal line intersects the resistors. In examples where the resistor is triangular except in regions where the resistor intersects the signal line, at the area of the resistor where the triangular shape transitions to the flat shape, the resistor may be shaped to match the contours of the surface of the signal line, such that no gap is present between the signal line and the resistor. However, in other examples, the resistor may have a transition to the flat region with a flat (non-contoured) edge of the triangular region, such that a small gap may be present at least partially between the resistor and signal line.

In FIG. 4, the contacts 70a-70f are shown as having substantially flat surfaces. Because the contacts represent a small portion of the inactive area, suitable photon redirection may be obtained without reshaping the contacts. In other examples, the contacts may have a desired 3D shape to further increase photon redirection to the active area, such as the contacts having a shape similar to the signal line. Additionally, the resistors may have a substantially flat shape in the regions where the contacts intersect the resistors (as shown in FIG. 4), or the contacts may be shaped to match the triangular shape of the resistors. Further still, the border of the microcell array, which may be devoid of resistors and contacts at least in some examples, may also be of triangular or other shape to redirect incident photons. In general, any area of the inactive region may be shaped to increase photon redirection to the active areas.

Figure 9:
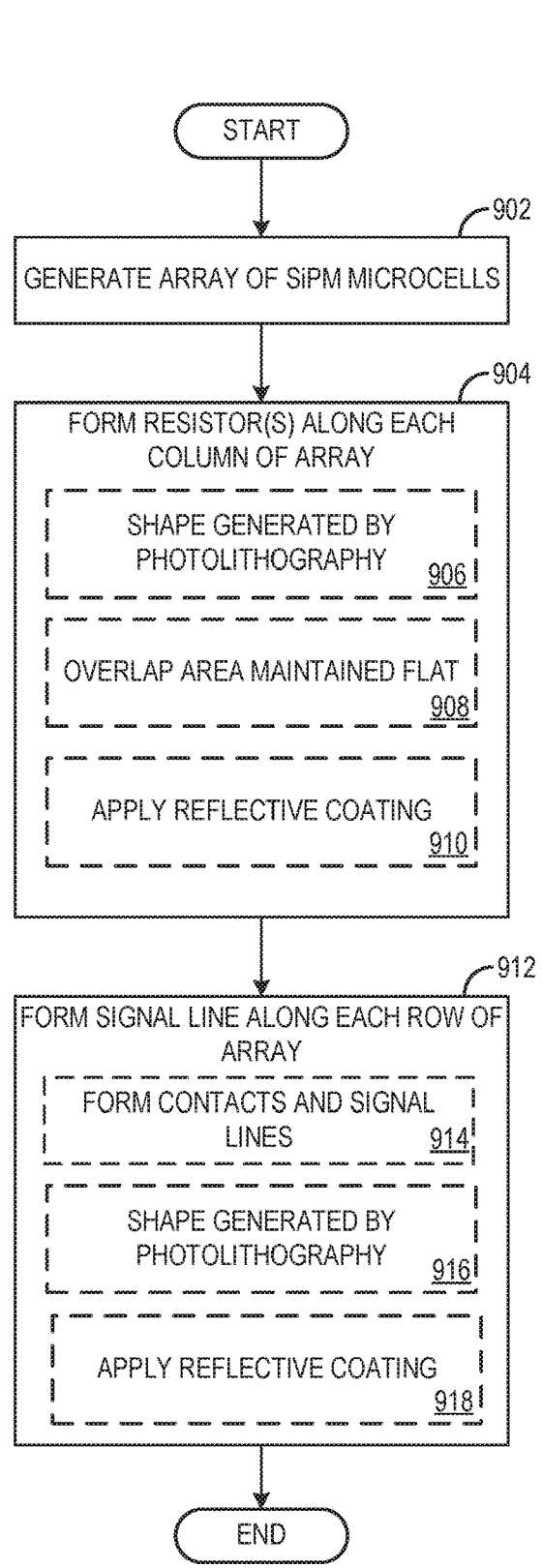
FIG. 9 is a method for manufacturing the microcell array of FIG. 4.

Turning now to FIG. 9, a method 900 for manufacturing a microcell array, such as the microcell array of FIG. 4, is shown. At 902, method 900 includes generating an array of microcells, such as the silicon photomultiplier (SiPM) microcells described above with respect to FIG. 4. The array of SiPM microcells may be formed in a suitable manner. In one example, the array may be formed by using photolithography to form P-doped wells in an N-doped common silicon body (e.g., wafer). For example, the N-doped silicon wafer may be coated in silicon dioxide via a thermal growth process. Then, a photoresist mask is spun on the silicon dioxide. The photoresist is exposed to ultraviolet light through a mask (e.g., a P-well mask) to generate a desired pattern. The exposed photoresist may then be removed with chemicals. The silicon dioxide that is now exposed may be removed with hydrofluoric acid or other suitable process. The remaining photoresist is then removed using a suitable acid mixture. The P-doped active areas (also referred to as the entrance windows or P-wells) may be formed by diffusion or ion implementation. Only the areas that do not have a silicon dioxide layer will form the P-wells; the areas under the silicon dioxide will remain n-type. Also, the P-doped active area may grow on top of the N-doped base area using an epitaxy process.

At 904, method 900 includes forming quenching resistors along each column of the array. The resistors may be formed by chemical vapor deposition (CVD) followed by photolithography. For example, a layer of silicon dioxide may be deposited over the array, followed by CVD of silicon. The silicon may be deposited in a relatively thick layer, to allow for the eventual formation of the triangular or trapezoidal cross-sectional shape of the resistors. The array may then be placed in a furnace with silane gas in order to form a layer of polysilicon.

The layer of polysilicon may be patterned in a manner similar to that of the formation of the p-wells. As such, a layer of silicon dioxide may be deposited on the polysilicon followed by a layer of photoresist. The photoresist may be exposed to UV light via a resistor mask, and the exposed photoresist and underlying silicon dioxide removed as described above. The exposed polysilicon is then removed using wet etching or other suitable technique.

As indicated at 906, the patterning of the photolithography process to remove the exposed polysilicon may be performed in a manner that generates suitably shaped resistors described above with respect to FIG. 6, such as triangular, in the form of a parallelogram, etc. In one example, a series of photolithography steps may be performed with different masks and different amounts of time in chemical etching. Further, as indicated at 908, the patterning of the photolithography process may be performed such that the region(s) of the resistors that will be positioned in contact/underneath the signal line(s) are flat rather than triangular shaped or in the form of a parallelogram with different masks and different amounts of time in chemical etching.

As indicated at 910, forming the resistors may further include forming a reflective layer. As explained above, the reflective layer may be formed of silicon nitride or aluminum on top of the resistors through a chemical vapor deposition, with the reflectivity of the reflective layer controlled by the thickness of the layer.

At 912, method 900 includes forming a signal line along each row (or every other row) of the array. As indicated at 914, forming the signal line along each row of the array (or every other row) may include forming the contacts and the signal lines. The signal lines may be formed from aluminum. The aluminum may be sputtered over the microcell in a relatively thick layer to allow for the eventual formation of the triangular (or parallelogram) shaped signal lines. The contacts may be formed from aluminum and may be formed at the same time the signal lines are formed. As indicated at 916, the shape of the signal lines may be generated by a photolithography process similar to that discussed above with respect to the formation of the resistors. For example, a series of masks may be used for multiple photolithography steps to form the triangular shape of the signal lines.

Forming the signal lines may also include applying a reflective coating, as indicated at 918. Aluminum itself has more than 90% reflectivity but a passivation layer on top of the signal line may be reflective layer. SiO2 or SiN may be vapor deposited to be a reflective layer by having a proper thickness as was performed for the resistors at 910. Method 900 then returns.

In this way, a silicon photomultiplier may be formed. The silicon photomultiplier may include a plurality of microcells, where each microcell includes an active area (e.g., a region of P-doped silicon formed in an N-doped silicon substrate) electrically coupled to a quenching resistor. The plurality of microcells may be arranged into an array, with subsets of the array coupled to respective signal lines. For example, each row of the array of microcells may be coupled to a respective signal line, or two rows of microcells may be coupled to a given signal line, or other suitable arrangement. Each microcell may be coupled to an associated signal line via its quenching resistor. The quenching resistors may be comprised of polysilicon or metal and the signal lines may be comprised of aluminum.

To redirect incident photons that may impinge on the signal lines and/or resistors to the active areas, the signal lines only (e.g., and not the quenching resistors) or both the signal lines and resistors may be shaped to redirect incident photons to the active areas, by having sides surfaces that extend vertically away from the microcells and that angle inward toward each other, such as triangles, parallelograms, rounded triangles, trapezoids, or other suitable shape that is configured to reflect photons to a nearby active area. As such, the signal lines and resistors may extend above the surface of the active areas by a suitable height, and the triangular or parallelogram shapes may have suitable steepness, to provide a desired amount of photon redirection. The signal lines and resistors may be formed in the triangular or parallelogram shape during manufacture of the silicon photomultiplier using a subtractive photolithography process.

While the photomultiplier described herein is a p-on-n semiconductor configuration comprised of silicon, other types of photomultipliers are possible, such as germanium, indium galleium arsinide, and so forth. Further, rather than being a p-on-n configuration, the photomultiplier may be comprised of n-on-p, p-n junctions, pin diodes, or other suitable configurations.

A technical effect of constructing photomultiplier signal lines and resistors to have 3-dimensional shapes adapted to reflect photons is to increase the photon detection efficiency of the photomultiplier without substantially increasing manufacturing costs or complexity.

An example provides a photomultiplier device including a microcell including an active area coupled to a quenching resistor; and a signal line coupled to the quenching resistor, the signal line including a first side surface, a second side surface, and a base, the first side surface and second side surface angled inward toward each other. In a first example, the signal line is comprised of aluminum without any additional layers. In a second example that optionally includes the first example, the first side surface and second side surface join to form a peak. In a third example that optionally includes one or more or both of the first and second examples, the signal line comprises a top surface positioned above the base and joining the first side surface and second side surface. In a fourth example that optionally includes one or more or each of the first through third examples, the signal line includes a first internal angle between the first side surface and base that is less than 90°, and wherein the signal line includes a second internal angle between the second side surface and base that is less than 90°. In a fifth example that optionally includes one or more or each of the first through fourth examples, the first internal angle and second internal angle are each greater than 45°. In a sixth example that optionally includes one or more or each of the first through fifth examples, the quenching resistor comprises an active quenching circuit. In a seventh example that optionally includes one or more or each of the first through sixth examples, the quenching resistor includes a first resistor side surface, second resistor side surface, and a resistor base, the first resistor side surface and second resistor side surface angled inward toward each other. In an eighth example that optionally includes one or more or each of the first through seventh examples, the quenching resistor comprises a polysilicon core and a reflective layer. In a ninth example that optionally includes one or more or each of the first through eighth examples, the quenching resistor comprises a metal resistor. In a tenth example that optionally includes one or more or each of the first through ninth examples, the active area comprises a P-doped silicon entrance window positioned in an N-doped silicon substrate. In an eleventh example that optionally includes one or more or each of the first through tenth examples, the device further includes an insulator positioned under the base of the signal line.

An example provides for a photomultiplier device including a plurality of microcells, each microcell comprising an active area; a plurality of quenching resistors, each respective quenching resistor coupled to a respective active area, each quenching resistor having a triangular shaped cross-section; and a signal line coupled to each quenching resistor, the signal line having a triangular shaped cross-section. In a first example, the signal line comprises aluminum. In a second example that optionally includes the first example, each quenching resistor comprises polysilicon and a reflective coating, the reflective coating comprising aluminum, silicon nitride, or silicon dioxide.

An example provides a medical imaging detector module including a scintillator configured to absorb ionizing radiation and convert the ionizing radiation into optical photons; and a photomultiplier coupled to the scintillator, the photomultiplier configured to receive the optical photons and to convert the optical photons into corresponding electrical signals, the photomultiplier including: a plurality of photon-sensitive active areas each surrounded by a photon-insensitive inactive area; a plurality of quenching resistors, each respective quenching resistor coupled to a respective active area and positioned over a portion of a respective inactive area; and a signal line coupled to each quenching resistor and positioned over another portion of a respective inactive area, the signal line including a first side surface, a second side surface, and a base, a first internal angle formed between the first side surface and the base being less than 90° and a second internal angle formed between the second side surface and the base being less than 90°. In a first example, the signal line is coupled to a data acquisition system configured to reconstruct one or more images from the electrical signals. In a second example that optionally includes the first example, each quenching resistor includes a first resistor side surface, a second resistor side surface, and a resistor base, a third internal angle formed between the first resistor side surface and the resistor base being less than 90° and a fourth internal angle formed between the second resistor side surface and the resistor base being less than 90°. In a third example that optionally includes one or more or each of the first and second examples, the signal line comprises aluminum, and wherein each quenching resistor comprises polysilicon and a reflective coating. In a fourth example that optionally includes one or more or each of the first through third examples, the first internal angle and second internal angle are each greater than 45°.

In another representation, a photomultiplier device includes a plurality of microcells, each microcell comprising an active area; a plurality of active quenching circuit, each respective active quenching circuit coupled to a respective active area; and a signal line coupled to each respective active quenching circuit, the signal line having a triangular shaped cross-section.

In another representation, a method for manufacturing a photomultiplier device comprises generating an array of photomultiplier cells; forming one or more resistors along each column of the array; and forming a signal line along each row or every other row of the array, where forming the signal lines includes forming each signal line into a three-dimensional shape using photolithography. The three-dimensional shape may include a triangular cross-sectional shape, trapezoidal cross-section shape, or a cross-sectional shape in the form of a parallelogram.

In an example, forming the signal lines may include forming signal lines by a sputtering aluminum on the array followed by photolithography. The forming of the signal lines using photolithography may include performing a series of photolithography steps with different masks and/or for different amounts of time of chemical etching to form the triangular cross-sectional shape, trapezoidal cross-section shape, or the cross-sectional shape in the form of a parallelogram. In an example, forming the one or more quenching resistors may include forming the one or more quenching resistors by a chemical vapor deposition process followed by photolithography. The forming of the one or more quenching resistors by CVD followed by photolithography may include patterning in the photolithography process to generate one or more quenching resistors having a triangular (or other shape) cross-sectional shape. The patterning may include a series of photolithography steps with different masks and for different amounts of time of chemical etching. The array of photomultiplier cells may be generated by a photolithography process to form P-doped wells in an N-doped common silicon body, such as a wafer. In an example, the photomultiplier cells may be generated by coating an N-doped silicon wafer in silicon dioxide, spinning a photoresist mask on the silicon dioxide, exposing the mask to UV light, removing the photoresist mask, removing the exposed silicon dioxide, and then removing the mask. P-wells may then be formed by diffusion or grown via epitaxy.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A photomultiplier device, comprising:
a microcell including an active area coupled to a quenching resistor, the quenching resistor positioned over an inactive area of the microcell and including a first resistor side surface, a second resistor side surface, and a resistor base, the first resistor side surface and the second resistor side surface angled inward toward each other; and
a signal line coupled to the quenching resistor, the signal line including a first side surface, a second side surface, and a base, the first side surface and the second side surface angled inward toward each other, the inactive area including a depletion region between adjacent P-doped silicon entrance windows.

2. The photomultiplier device of claim 1, wherein the signal line is comprised of aluminum without any additional layers.

3. The photomultiplier device of claim 1, wherein the first side surface and the second side surface join to form a peak, and wherein the active area comprises four sides, the signal line extending along only a first side of the four sides and the quenching resistor extending along only a second side of the four sides.

4. The photomultiplier device of claim 1, wherein the signal line comprises a top surface positioned above the base and joining the first side surface and the second side surface.

5. The photomultiplier device of claim 1, wherein the signal line includes a first internal angle between the first side surface and the base that is less than 90°, and wherein the signal line includes a second internal angle between the second side surface and the base that is less than 90°.

6. The photomultiplier device of claim 5, wherein the first internal angle and the second internal angle are each greater than 45°.

7. The photomultiplier device of claim 1, wherein the quenching resistor comprises a polysilicon core and a reflective layer.

8. The photomultiplier device of claim 1, wherein the quenching resistor comprises a metal resistor.

9. The photomultiplier device of claim 1, wherein the active area comprises one of the adjacent P-doped silicon entrance windows positioned in an N-doped silicon substrate.

10. The photomultiplier device of claim 1, wherein the inactive area comprises an insulator, the insulator also positioned under the base of the signal line, and wherein the first resistor side surface and the second resistor side surface form a peak centered over a center of the inactive area.

11. A photomultiplier device, comprising:
a plurality of microcells, each microcell comprising an active area;
a plurality of quenching resistors, each respective quenching resistor coupled to a respective active area and positioned over a respective inactive area, and each quenching resistor having a triangular shaped cross-section; and
a signal line coupled to each quenching resistor, the signal line having a triangular shaped cross-section, each respective inactive area including a depletion region between two adjacent P-doped silicon entrance windows.

12. The photomultiplier device of claim 11, wherein the signal line comprises aluminum, wherein the plurality of quenching resistors includes a first quenching resistor coupled to a first active area, the first active area having four sides and the first quenching resistor extending along only a first side of the four sides, and the signal line extending along the first active area only at a second side of the four sides in a direction perpendicular to a direction of the first quenching resistor.

13. The photomultiplier device of claim 12, wherein each quenching resistor comprises polysilicon and a reflective coating, the reflective coating comprising aluminum, silicon nitride, or silicon dioxide, and wherein the triangular shaped cross-section of the first quenching resistor is formed from a first resistor side surface and a second resistor side surface angled to form a peak, the peak centered over a first inactive area and the first resistor side surface extending from the peak to the first active area and the second resistor side surface extending from the peak to a second active area.

* * * * *